(12) United States Patent
Li et al.

(10) Patent No.: US 10,967,570 B2
(45) Date of Patent: Apr. 6, 2021

(54) DEVICE FOR PRINTING LUMEN TISSUE CONSTRUCT, METHOD FOR USING THE SAME AND 3D BIOPRINTER

(71) Applicant: REVOTEK CO., LTD, Sichuan (CN)

(72) Inventors: Yijun Li, Sichuan (CN); Junxuan He, Sichuan (CN); Zhi Jiang, Sichuan (CN); Xiaolin Hu, Sichuan (CN); Leqing Zhang, Sichuan (CN); Deming Wang, Sichuan (CN)

(73) Assignee: REVOTEK CO., LTD, Chengdu (CN)

( * ) Notice: Subject to any disclaimer, the term of this patent is extended or adjusted under 35 U.S.C. 154(b) by 180 days.

(21) Appl. No.: 15/964,214

(22) Filed: Apr. 27, 2018

(65) Prior Publication Data

US 2019/0217537 A1    Jul. 18, 2019

(30) Foreign Application Priority Data

Jan. 18, 2018    (CN) .......................... 201810048700.6

(51) Int. Cl.
| | |
|---|---|
| *B29C 64/209* | (2017.01) |
| *A61L 27/50* | (2006.01) |
| *B29C 64/245* | (2017.01) |
| *B29C 64/295* | (2017.01) |
| *B33Y 30/00* | (2015.01) |
| *A61F 2/06* | (2013.01) |

(Continued)

(52) U.S. Cl.
CPC .............. *B29C 64/209* (2017.08); *A61F 2/06* (2013.01); *A61F 2/2415* (2013.01); *A61L 27/507* (2013.01); *B29C 64/124* (2017.08); *B29C 64/245* (2017.08); *B29C 64/295* (2017.08); *B33Y 10/00* (2014.12); *B33Y 30/00* (2014.12); *B29L 2031/753* (2013.01); *B33Y 80/00* (2014.12)

(58) Field of Classification Search
CPC ... B29C 64/295; B29C 64/245; B29C 64/209; B29C 64/124; B29L 2031/753; A61F 2/06; A61F 2/2415; B33Y 80/00; B33Y 30/00; B33Y 10/00; A61L 27/507
See application file for complete search history.

(56) References Cited

U.S. PATENT DOCUMENTS

| | | | |
|---|---|---|---|
| 2003/0211130 A1* | 11/2003 | Sanders | ................... A61L 27/34 |
| | | | 424/423 |
| 2010/0330144 A1* | 12/2010 | Liu | ......................... B29C 48/36 |
| | | | 424/423 |
| 2016/0361869 A1* | 12/2016 | Mark | ...................... B29C 48/92 |

FOREIGN PATENT DOCUMENTS

| | | |
|---|---|---|
| WO | 2016/154882 A1 | 10/2016 |
| WO | 2016/201577 A1 | 12/2016 |

OTHER PUBLICATIONS

European Extended Search Report dated Feb. 22, 2019 received in European Patent Application No. 18 17 1137.5.

* cited by examiner

*Primary Examiner* — Christine H Matthews
*Assistant Examiner* — Joshua Daryl D Lannu
(74) *Attorney, Agent, or Firm* — Scully Scott Murphy & Presser

(57) ABSTRACT

A device and method for printing lumen tissue constructs and a 3D bioprinter are disclosed. The device has a spray sprayhead assembly and a bioprinting platform. The spray sprayhead assembly prints a biological construct on an inner surface of a lumen tissue by the bioprinting platform. Problems, such as, recurrence of thrombus and restenosis of a lumen after the lumen tissue has been transplanted for a long time, can be avoided. The biological reliability of the lumen tissue can be improved.

25 Claims, 8 Drawing Sheets

(51) Int. Cl.
  *B29C 64/124*   (2017.01)
  *A61F 2/24*   (2006.01)
  *B33Y 10/00*   (2015.01)
  *B29L 31/00*   (2006.01)
  *B33Y 80/00*   (2015.01)

DEVICE FOR PRINTING LUMEN TISSUE CONSTRUCT, METHOD FOR USING THE SAME AND 3D BIOPRINTER

CROSS REFERENCE TO RELATED APPLICATION

The present application claims priority from Chinese application number CN201810048700.6 filed Jan. 18, 2018, which is herein incorporated by reference.

FIELD OF THE DISCLOSURE

The present invention relates to the technical field of 3D bioprinting, and especially relates to a device for printing lumen tissue construct, a method for using the same and a 3D bioprinter.

BACKGROUND

In the prior art, common artificial blood vessels are made from polymer fibers (e.g., nylon, dacron), silk, or ePTFE. In the case of vascular transplantation, intact artificial blood vessels may be used to replace lesioned or damaged blood vessels. Although the replacement of lesioned or damaged blood vessels with such artificial blood vessels has attained great clinical achievement, it is still confronted with difficult problems, including recurrence of thrombus and appearance of restenosis of a lumen after transplantation for a long time. The root of these problems lies in the lack of a complete endothelial cell layer on the inner surface of such artificial blood vessels.

In addition, since the artificial blood vessels can hardly deform in a radial direction, the prior art cannot externally compress the artificial blood vessels so that the bio-block is completely evenly, intactly, and flatly attached on the inner wall of the artificial blood vessels.

SUMMARY

In order to overcome the above technical defects, the technical problem solved by the present invention is to provide a device for printing lumen tissue construct, a method for using the same and a 3D bioprinter, aiming at improving the biological reliability of the lumen tissue.

In order to solve the above technical problem, the present invention provides a device for printing lumen tissue construct, which comprises a sprayhead assembly and a bioprinting platform, the sprayhead assembly prints a biological construct on an inner surface of a lumen tissue by the bioprinting platform.

Further, the sprayhead assembly includes a medical adhesive sprayhead, which consist of a medical adhesive container and a medical adhesive nozzle, wherein a top of the medical adhesive container is connected with an air pump through an air path, in which a vacuum generator is provided for generating a negative pressure for the medical adhesive container in a non-printing state.

Further, the sprayhead assembly includes a bio-block sprayhead which consist of a screw pump and a bio-block nozzle.

Further, the screw pump includes a spiral stator and a spiral rotor for extruding a bio-block entering the screw pump to the bio-block nozzle, wherein the spiral stator is made of a silicone material.

Further, a printing outlet end of the bio-block nozzle has a chamfer, which has a chamfered surface defining an included angle of 10° to 30° with a center line of a printing outlet of the bio-block nozzle.

Further, the included angle is 20°.

Further, an outer surface at the printing outlet end of the bio-block nozzle has a roughness Ra≤0.4.

Further, the bioprinting platform includes a platform base, a rotary part and a butt-jointed part movable relative to the rotary part, the rotary part includes a rotary rod for placing the bio-block and the medical adhesive to form a biological construct, and the butt-jointed part includes a hollow rod having an outer wall for placing the lumen tissue.

Further, the outer wall of the rotary rod is covered with an elastic film.

Further, an interior of the rotary rod is hollow, and the outer wall of the rotary rod is provided with a vent communicating with the interior, for exhausting air inside the rotary rod to balloon the elastic film.

Further, the interior of the rotary rod is provided with a heating unit.

Further, the heating unit includes a heating section and a spacing section that are spacedly arranged, wherein the heating section has a surface wound with a resistance wire, and the heating section has a diameter that is less than that of the spacing section.

Further, a temperature detecting unit is provided at one end of the heating unit proximate to the butt-jointed part, for detecting the temperature of the heating unit.

Further, the bioprinting platform includes a gripping mechanism for gripping the lumen tissue to make it disengaged from the hollow rod and socketed to the biological construct.

Further, the gripping mechanism includes a first gripping block and a second gripping block which are movable relatively.

Further, the gripping mechanism includes a retaining unit for acting on a tail end of the lumen tissue so that it is disengaged from the hollow rod.

Further, the retaining unit is cooperatively provided with a retaining ring acting on the tail end of the lumen tissue.

Further, the gripping mechanism includes a limiting block provided at the bottom of the first gripping block and the second gripping block, for limiting relative movement of the first gripping block and the second gripping block, so that the first gripping block and the second gripping block are both tangent to the outer wall of the lumen tissue.

Further, the gripping mechanism includes a support platform provided at the bottom of the first gripping block and the second gripping block, for supporting the lumen tissue.

Further, the device comprises an optical probe movable inside the rotary rod, for detecting the flatness of the inner wall of the biological construct, wherein the rotary rod is made of a transparent material.

Further, the optical probe is movably disposed within the rotary rod or the hollow rod.

Further, the optical probe is fixedly disposed within the hollow rod.

Further, there further comprises a reservoir provided below the rotary rod, for bearing a bioprinting construct disengaged and falling from the gripping mechanism.

The present invention further provides a 3D bioprinter, which comprises the aforementioned device for printing lumen tissue construct.

The present invention further correspondingly provides a method of printing lumen tissue construct using the aforementioned device, which comprises a mantling step: cladding a layer of elastic film on the outer wall of the rotary rod before printing the biological construct.

Further, there further comprises a ballooning step: ventilating into the elastic film to balloon the elastic film so that the biological construct is attached to the inner wall of the lumen tissue, after the lumen tissue is sleeved outside the biological construct.

Therefore, based on the aforementioned technical solution, the device for printing lumen tissue construct of the present invention provides the sprayhead assembly and the bioprinting platform, and the sprayhead assembly prints the biological construct on the inner surface of the lumen tissue by the bioprinting platform, thus avoid such problems as recurrence of thrombus and restenosis of a lumen after the lumen tissue has been transplanted for a long time, thereby improving the biological reliability of the lumen tissue. The method of printing lumen tissue construct and the 3D bioprinter provided by the present invention also correspondingly have the advantageous technical effects described above.

BRIEF DESCRIPTION OF THE ACCOMPANYING DRAWINGS

The drawings described herein are used to provide a further understanding of the present invention and constitute a part of the present application. The illustrative embodiments of the present invention as well as the descriptions thereof, which are merely used for explaining the present invention, and do not constitute improper definitions on the present invention. In the drawings.

Various reference signs respectively represent:
1. sprayhead assembly; 11. medical adhesive sprayhead; 111. medical adhesive container; 112. medical adhesive nozzle; 113. medical adhesive piston; 12. bio-block sprayhead; 121. screw pump; 1211. spiral stator; 1212. spiral rotor; 1213. inlet connecting piece; 122. bio-block nozzle; 123. thermal insulation shell; 124. bio-block piston; 125. bio-block container; 126. semiconductor cooling plate; 127. connecting tube; 128. bio-block inlet; 129. thermal insulation sleeve; 2. bioprinting platform; 21. rotary part; 211. rotary rod; 212. heating unit; 2121. heating section; 2122. connecting groove; 2123. spacing section; 213. temperature detecting unit; 214. sealing ring; 22. gripping mechanism; 221, 221'. first gripping block; 222, 222'. second gripping block; 223, 223'. retaining unit; 224. support platform; 225. limiting block; 23. butt-jointed part; 231. hollow rod; 232. displacement mechanism.

DETAILED DESCRIPTION

Next, the technical solution of the present invention is further described in detail by means of the drawings and embodiments.

The specific embodiments of the present invention are further described in order to facilitate understanding of the concept of the present invention, the technical problem to be solved, the technical features constituting the technical solution and the technical effect produced therefrom. It is necessary to explain that, the explanations for such embodiments do not constitute definitions on the present invention. In addition, the technical features involved in the embodiments of the present invention described below may be combined with each other as long as they do not constitute a conflict therebetween.

Figure 1:
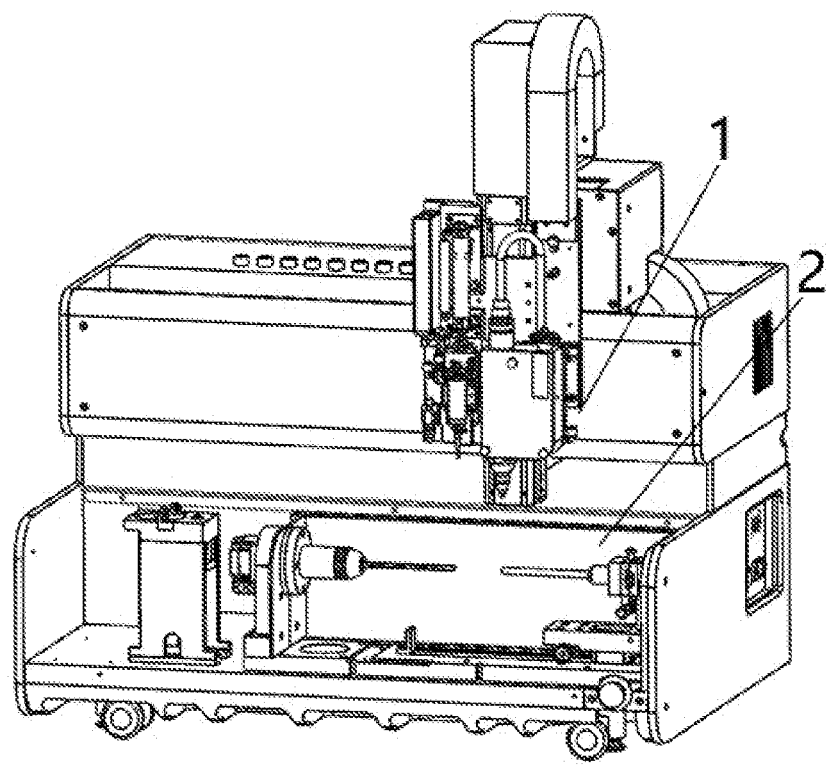
FIG. 1 illustrates an overall structure of the device for printing lumen tissue construct according to an embodiment of the present invention.

In an illustrative embodiment of the device for printing lumen tissue construct of the present invention, as shown in FIG. 1, the device comprises a sprayhead assembly 1 and a bioprinting platform 2, the sprayhead assembly 1 prints a biological construct on an inner surface of a lumen tissue by the bioprinting platform 2.

In the illustrative embodiment, the device provides the sprayhead assembly 1 and the bioprinting platform 2, and the sprayhead assembly 1 prints the biological construct on the inner surface of the lumen tissue by the bioprinting platform 2, thus avoid such problems as recurrence of thrombus and restenosis of a lumen after the lumen tissue has been transplanted for a long time, thereby improving the biological reliability of the lumen tissue. Among them, the lumen tissue is especially an artificial blood vessel, such as a commercial blood vessel of Gore, and the occurrence of thrombus after an artificial blood vessel has been transplanted for a long time may be avoided by printing the biological construct on the inner surface of the artificial blood vessel.

Figure 2:
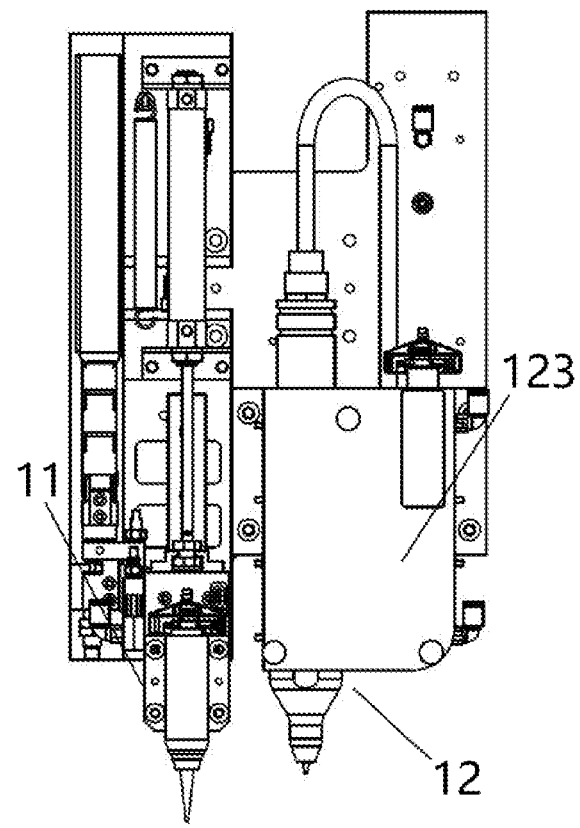
FIG. 2 illustrates an overall structure of a sprayhead assembly of the device according to an embodiment of the present invention.
Figure 3:
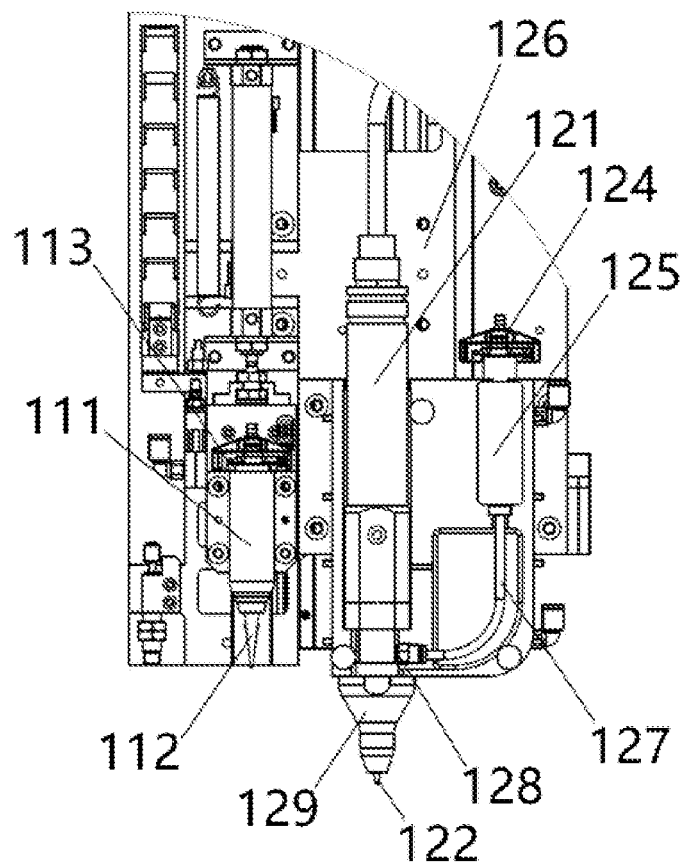
FIG. 3 illustrates an interior structure of a sprayhead assembly of the device according to an embodiment of the present invention.

In an improved embodiment of the device for printing lumen tissue construct of the present invention, as shown in FIGS. 2 and 3, the sprayhead assembly 1 includes a medical adhesive sprayhead 11, which consist of a medical adhesive container 111 and a medical adhesive nozzle 112, wherein the medical adhesive container 111 is used for containing a medical adhesive, the medical adhesive nozzle 112 is directly connected with the medical adhesive container 111, a top of the medical adhesive container 111 is connected with an air pump through an air path, in which a vacuum generator is provided for generating a negative pressure for the medical adhesive container 111 in a non-printing state. Since the medical adhesive presents an excellent fluidity, in a non-printing state, the medical adhesive may also drip slowly due to the effect of gravity. Thus, a vacuum generator is added in the air path, where certain negative pressure is present in a non-printing state, and the negative pressure counteracts with the gravity so that the medical adhesive no longer drips freely. Specifically or further, as shown in FIG. 3, a top of the medical adhesive container 111 is provided with a medical adhesive piston 113 which is connected with the air pump through an air path. The air pump is pressurized to extrude the medical adhesive from an ink bladder, and the vacuum generator is located between the air pump and the medical adhesive piston 113.

Figure 4:
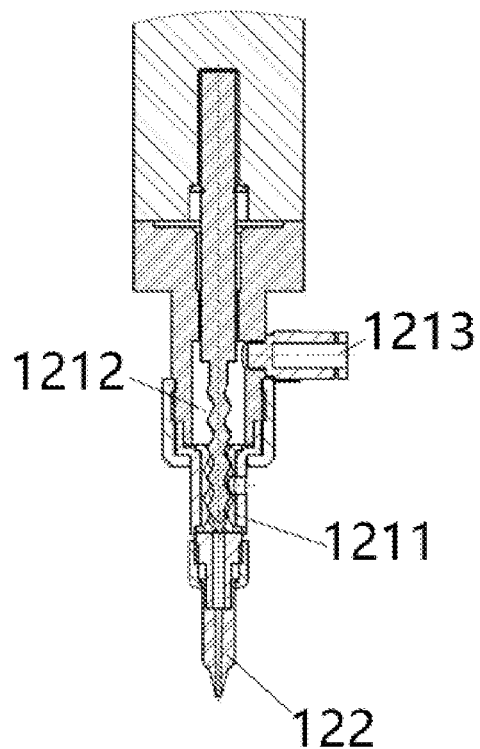
FIG. 4 illustrates a sectional structure of a screw pump of the device according to an embodiment of the present invention.

In an improved embodiment of the device for printing lumen tissue construct of the present invention, as shown in FIGS. 2 to 4, the sprayhead assembly 1 includes a bio-block sprayhead 12 which consist of a screw pump 121, a bio-block nozzle 122, and a bio-block container 125. The bio-block container 125 is used for containing bio-ink (bio-block). The outlet at the bottom of the bio-block container 125 communicates with the bio-block inlet 128 of the screw pump 121 through the connecting tube 127 and the inlet connecting piece 1213. The top of the bio-block container 125 is provided with a bio-block piston 124 which is connected with the air pump through an air path. The air pump is pressurized to extrude the bio-ink from the bio-block container 125 into the screw pump 121. The screw pump 121 includes a spiral stator 1211 and a spiral rotor 1212 for extruding a bio-block entering the screw pump 121 to the bio-block nozzle 122, wherein the spiral stator 1211 is made of a silicone material.

Due to the physical properties of the bio-block, when it is very small at the outlet of the bio-block container 125, the bio-block cannot be extruded and may form an accumulation at the outlet. Even if the pressure is increased, the bio-block cannot be extruded even if it is crushed. Likewise, even if such means as angular design is performed at the outlet of the bio-block container 125, the bio-block still cannot be extruded. However, the printing requirement defines that the bio-block cannot be extruded in large quantities, and only a few amount can be extruded at a time. Therefore, the bio-blocks can only be conveyed from the bio-block container 125 to the screw pump 121 and extruded by the screw pump 121. As the outlet of the screw pump 121 itself is very large, and the amount of the bio-blocks extruded each time is still greater than the operational requirement, a bio-block nozzle 122 is provided at the outlet of the screw pump 121.

As shown in FIG. 4, the spiral stator 1211 cannot rotate, the spiral rotor 1212 rotates relative to the spiral stator 1211, and the groove on the spiral rotor 1212 forms a chamber in which only a few amount of bio-blocks can be loaded within each chamber. The bio-blocks are conveyed out to the bio-block nozzle 122 along with rotation of the spiral rotor 1212. Due to the physical properties of the current bio-ink materials, the printing needs to be performed at a low temperature (4° C.). The screw stators of the existing screw pumps are made of a rubber material, which may rapidly age at a low temperature, so that black powder appears during the printing. The present invention makes a modification by making the spiral stator 1211 of silicone, thus avoiding the appearance of black powder during the printing.

Figure 5:
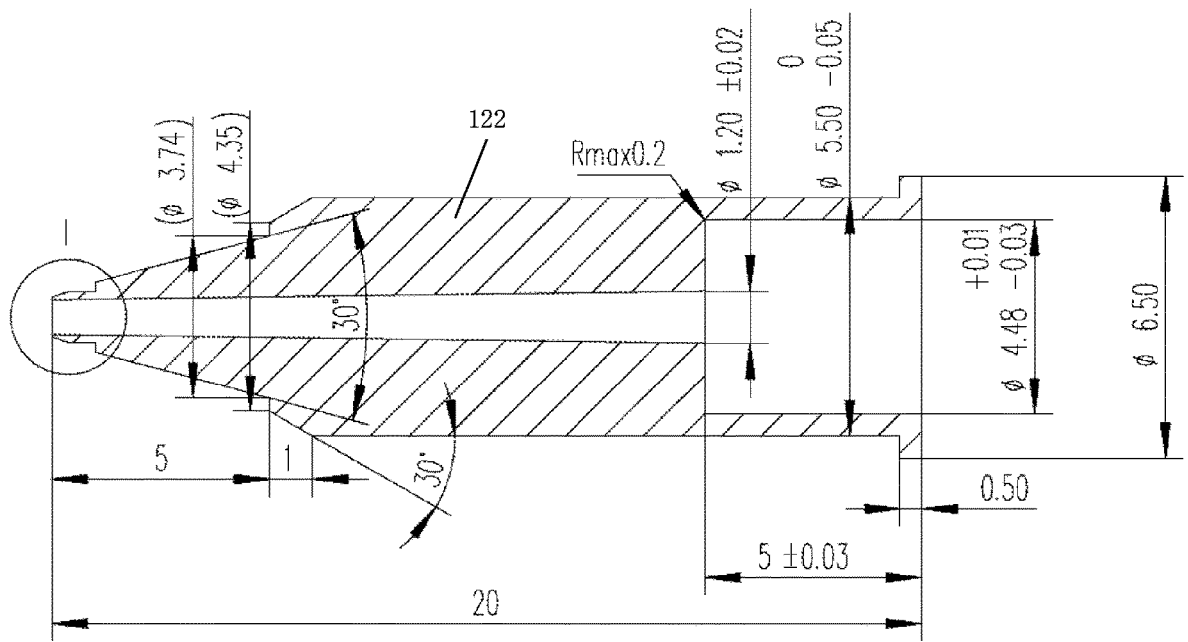
FIG. 5 illustrates a sectional structure of a bio-block nozzle of the device according to an embodiment of the present invention.
Figure 6:
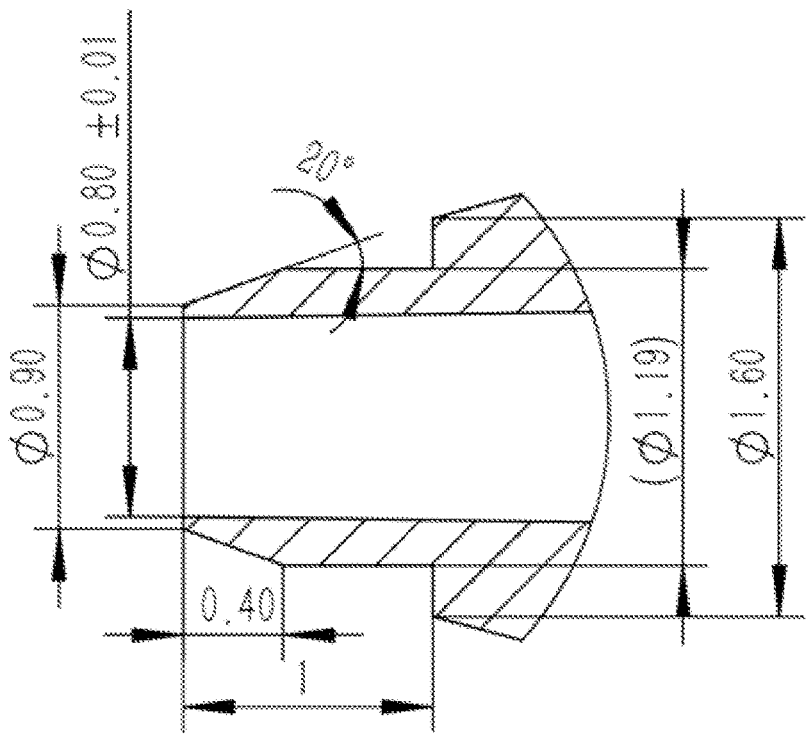
FIG. 6 is a locally enlarged schematic view of a circled portion in FIG. 5.

In order to avoid the phenomenon of "hanging droplets" (Due to high viscosity of the bio-ink, the bio-block after being extruded may not drip directly, but hang at the nozzle outlet. When a following bio-block is extruded, a previous bio-block that does not drip is piled up with the following to become a large droplet hanging at the outlet of the nozzle which may drip when the gravity of such large droplet is greater than the frictional force) appearing at a front end outlet (a circled portion in FIG. 5) of the bio-block nozzle 122 when printing the bio-block. In an improved embodiment, on one hand, as shown in FIGS. 5 and 6, a printing outlet end of the bio-block nozzle 122 has a chamfer, which has a chamfered surface defining an included angle of 10° to 30° with a center line of a printing outlet of the bio-block nozzle 122. Even further, the included angle is 20°, such design can effectively avoid the phenomenon of "hanging droplets". On the other end, an outer surface at the printing outlet end of the bio-block nozzle 122 has a roughness Ra≤0.4. The outer surface of the bio-block nozzle 122 may be plated/polished so as to increase the surface smoothness, and such design can be able to better avoid the phenomenon of "hanging droplets".

Since the currently used bio-ink may tend to coagulate in the case of a temperature greater than 4° C., it is very necessary to maintain the bio-block sprayhead at an ambient temperature of 4° C. In some improved embodiments, as shown in FIG. 3, the bio-block sprayhead 12 also includes a semiconductor cooling plate 126 located behind the screw pump 121 and the bio-block container 125, which can cool the bio-block sprayhead 12 by heat transfer. Further, as shown in FIG. 3, the bio-block nozzle 122 is externally provided with a thermal insulation sleeve 129. There is certain gap between the thermal insulation sleeve 129 and an exterior of the bio-block nozzle 122, in which an air thermal insulation layer can be formed. Further, as shown in FIG. 2, the screw pump 121 and the bio-block container 125 are externally sleeved with a thermal insulation shell 123 including a box cover and thermal insulation cotton covered on the outer surface of the box cover. The thermal insulation cotton can further improve the thermal insulation effect, and reduce the heat exchange between the sprayhead and the environment. The box cover is provided with a transparent window for observing the containing condition of the bio-ink in the bio-block container 125.

In some improved embodiments, the device further comprises a displacement assembly for moving the sprayhead assembly 1, and an entirety of the sprayhead assembly 1 (the bio-block sprayhead 12 and the medical adhesive sprayhead 11) may be displaced in a vertical direction and a horizontal direction, and the medical adhesive sprayhead 11 may be lifted independently. When the sprayhead assembly 1 is in the initial state, the horizontal position at the outlet of the bio-block sprayhead 12 is below the horizontal position at the outlet of the medical adhesive sprayhead 11. After the displacement assembly lowers the sprayhead assembly 1 to certain height during the printing, the bio-block sprayhead 12 extrudes the bio-block, and wholly ascends a segment after the printing of the lumen tissue is accomplished, then the medical adhesive sprayhead 11 descends independently, to print the medical adhesive.

Figure 7:
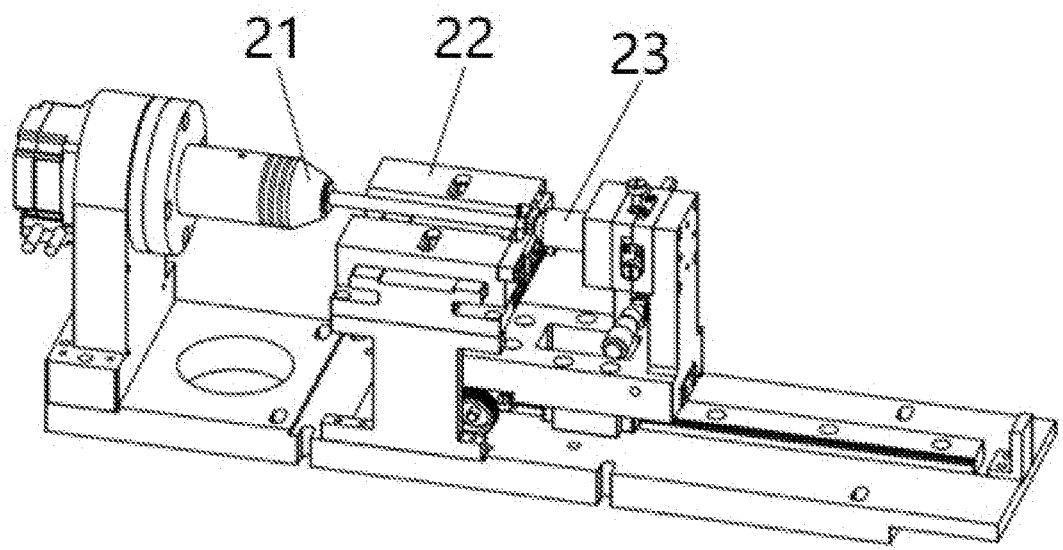
FIG. 7 illustrates an overall structure of a bioprinting platform of the device according to an embodiment of the present invention.
Figure 8:
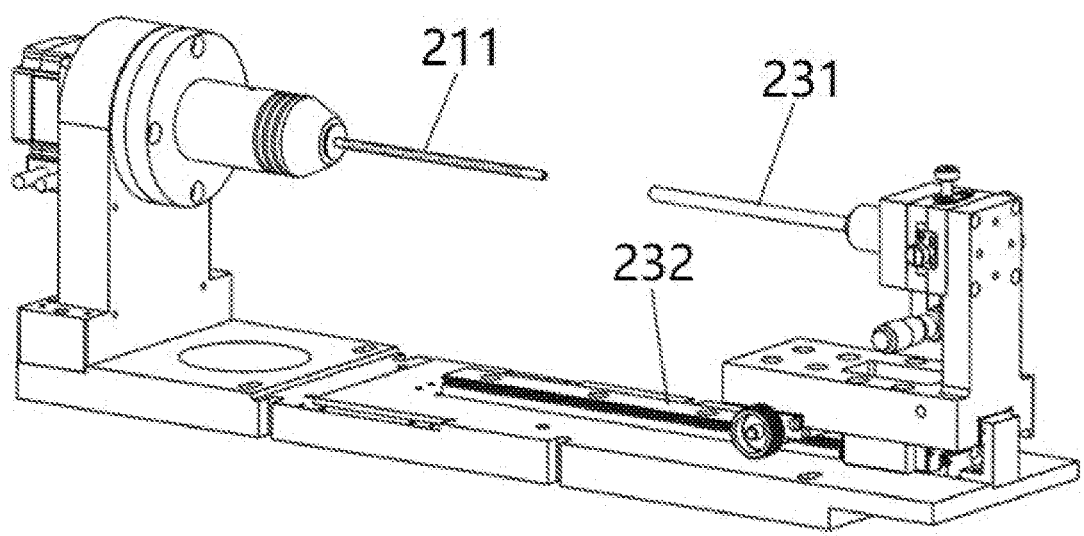
FIG. 8 illustrates a local structure of a bioprinting platform of the device according to an embodiment of the present invention.

In an improved embodiment of the device for printing lumen tissue construct of the present invention, as shown in FIGS. 7 and 8, the bioprinting platform 2 includes a platform base, a rotary part 21 and a butt-jointed part 23 movable relative to the rotary part 21, wherein the rotary part 21 includes a rotary rod 211 for placing the bio-block and the medical adhesive to form a biological construct, and the butt-jointed part 23 includes a displacement mechanism 232 and a hollow rod 231 having an outer wall for placing the lumen tissue and having an inner cavity for containing the rotary rod 211 with the biological construct.

Figure 9:
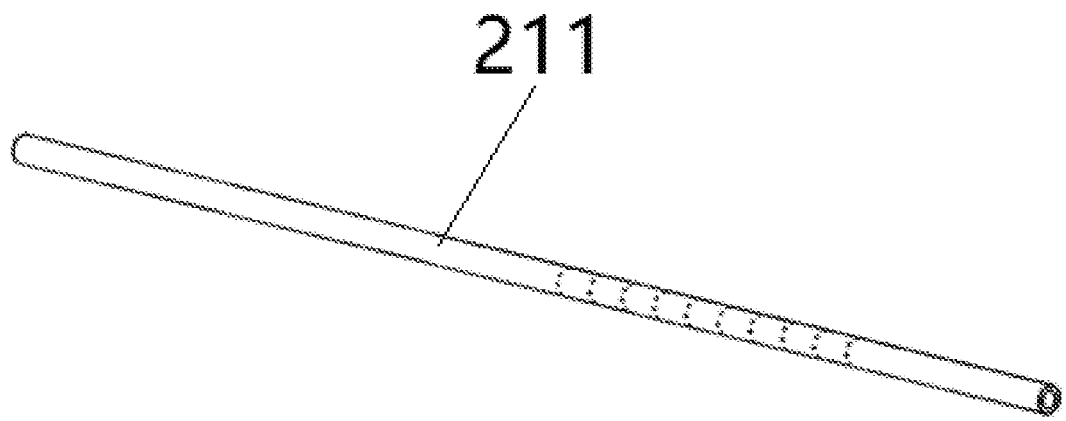
FIG. 9 illustrates the structure of a rotary rod of the device according to an embodiment of the present invention.
Figure 12:
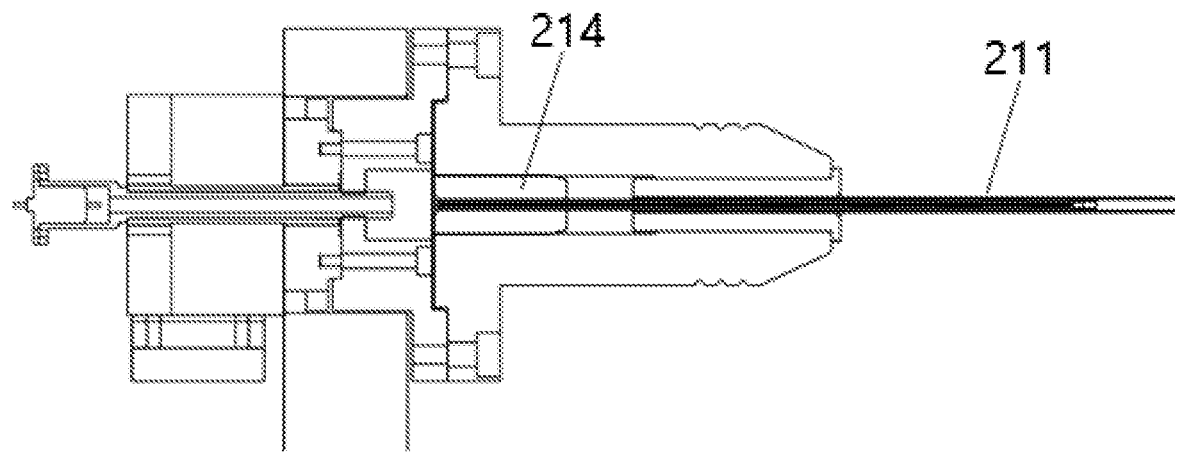
FIG. 12 illustrates an interior structure of a rotary part of the device according to an embodiment of the present invention.

After the biological construct is manufactured on the rotary rod 211, the hollow rod 231 is displaced toward a direction of the rotary part 21 driven by the displacement mechanism 232. The rotary rod 211 together with the biological construct enter the inner cavity of the hollow rod 231, and the lumen tissue sleeved outside the hollow rod 231 is displaced to the outside of the biological construct along with the hollow rod 231. Further, the surface of the hollow rod 231 is plated with a Teflon layer, which is capable of avoiding that the medical adhesive contacts and reacts with the metal surface. The hollow rod 231 is further displaced in an opposite direction driven by the displacement mechanism 232, and the lumen tissue is removed from the hollow rod 231, and then sleeved on the outer surface of the biological construct, so that the assembly is accomplished to obtain an artificial tissue precursor. Further, the outer wall of the rotary rod 211 is covered with an elastic film. During the printing of the biological construct, the elastic film presents a natural state and clads on the surface of the rotary rod 211. The bio-block makes up a biological construct on the surface of the elastic film, thus favorable for removing the biological construct. Further, as shown in FIG. 9, an interior of the rotary rod 211 is hollow, and the outer wall of the rotary rod 211 is provided with a vent communicating with the interior, for exhausting air inside the rotary rod 211 to balloon the elastic film. During the assembly of the biological construct and the lumen tissue, the rotary rod 211 is internally ventilated so that air expands outwards from the air outlet to balloon the elastic film (conceivably like a balloon is blown up). The biological construct on the surface of the elastic film is displaced outwards along with the expansion of the elastic film, and finally in contact with the inner wall of the lumen tissue and then adhered onto the inner wall of the lumen tissue, to obtain an artificial tissue precursor. It is demonstrated in practice that, the embodiment is easy to operate and implement, and presents a high implementability. Specifically or further, as shown in FIG. 12, a sealing ring 214 is provided inside the rotary part 21. The rotary rod 211 is detachably connected with the sealing ring 214, and the sealing ring 214 is used for sealing the inner cavity of the rotary rod 211, so that the process of balloon the elastic film is more controllable.

Figure 10:
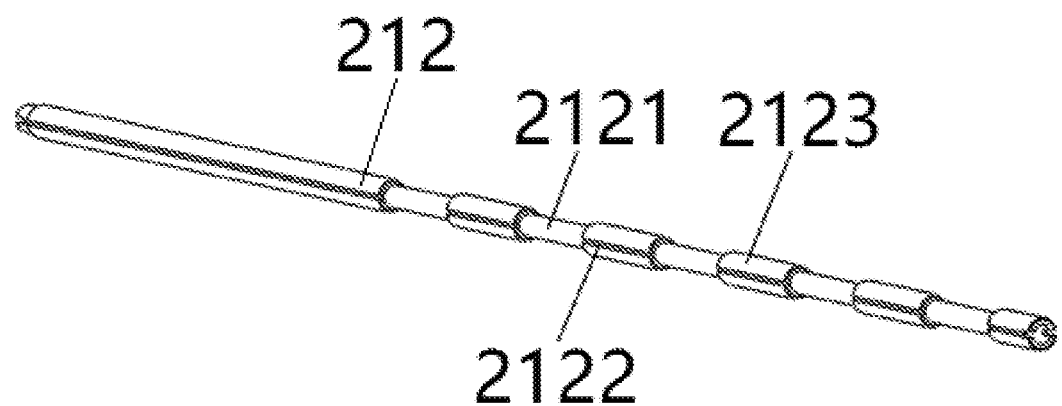
FIG. 10 illustrates the structure of a heating unit of the device according to an embodiment of the present invention.
Figure 11:
FIG. 11 illustrates the structure of a heating unit disposed inside the rotary rod of the device according to an embodiment of the present invention.

As an improvement to the above embodiment, as shown in FIGS. 10 and 11, the interior of the rotary rod 211 is further provided with a heating unit 212. The heating unit 212 can accelerate the coagulation rate of the bio-ink and shorten the preparation time of the bio-construct. The heating unit 212 needs to maintain the surface temperature of the rotary rod at 37° C.-38° C. Further, as shown in FIG. 11, a temperature detecting unit 213 is provided at one end of the heating unit 212 proximate to the butt-jointed part 23, for detecting the temperature of the heating unit 212, so as to maintain the surface temperature of the rotary rod in real time.

In a specific or improved embodiment, as shown in FIGS. 10 and 11, the heating unit 212 includes a heating section 2121 and a spacing section 2123 that are spacedly arranged, wherein a connecting groove 2122 is opened in the surface of the spacing section 2123, and the surface of the heating section 2121 is wounded with a resistance wire, the surface of the spacing section 2123 is not wounded with a resistance wire, the resistance wire between adjacent heating sections 2121 passes through the connecting groove 2122, and the diameter of the heating section 2121 is less than that of the spacing section 2123. The heating unit 212 is in clearance fit with the rotary rod 211, and the outer wall of the spacing section 2123 is in contact with the inner wall of the rotary rod 211. The purpose of providing the spacing section is to protect the resistance wire when the heating unit 212 is inserted into the rotary rod 211, so as to avoid that the resistance wire is damaged during the assembly.

As to how to remove the lumen tissue from the hollow rod 231, in an improved embodiment, as shown in FIG. 7, the bioprinting platform 2 further includes a gripping mechanism 22 for gripping the lumen tissue to make it disengaged from the hollow rod 231 and socketed to the biological construct when the hollow rod 231 is displaced in an opposite direction. The embodiment is easy to implement and has a high reliability.

Figure 13:
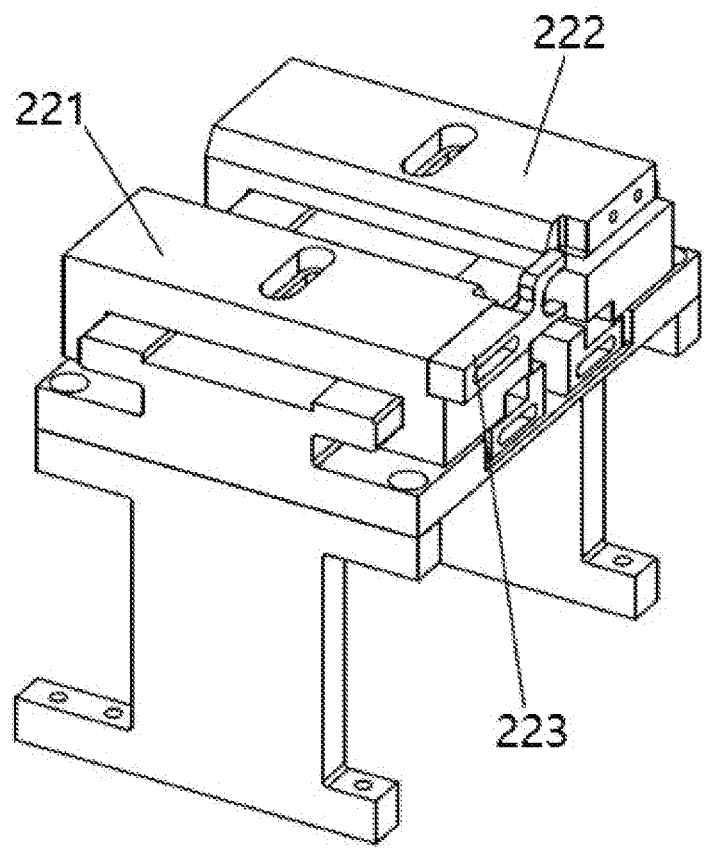
FIG. 13 illustrates the structure of a first embodiment of a gripping mechanism of the device according to the present invention.
Figure 14:
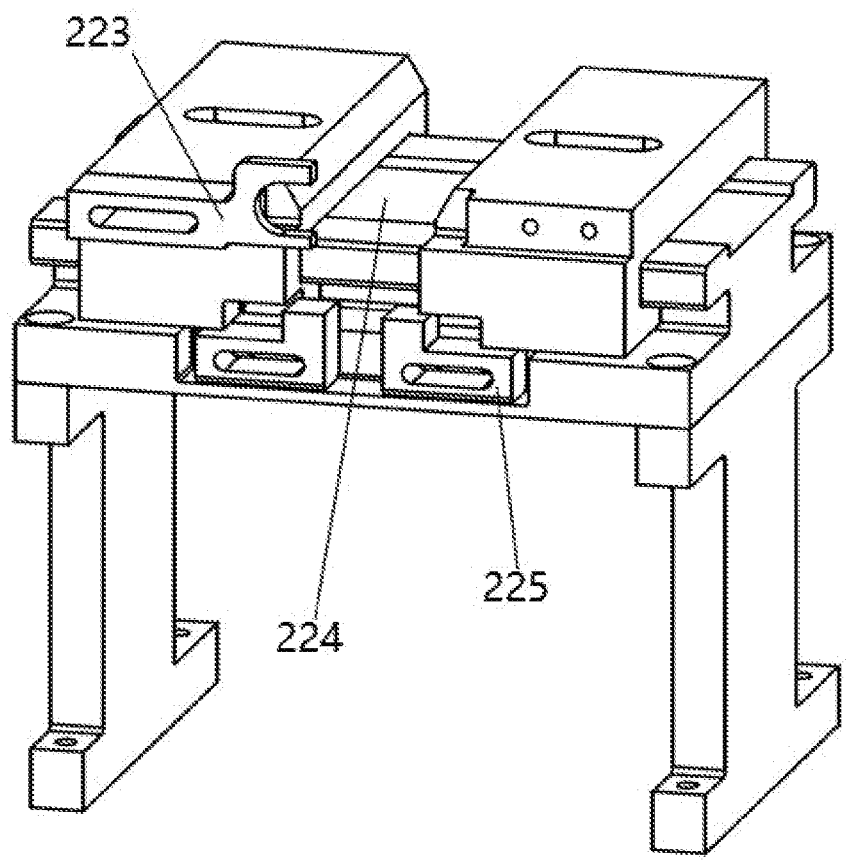
FIG. 14 illustrates the structure of a first embodiment of a gripping mechanism of the device according to the present invention in another angle of view.
Figure 15:
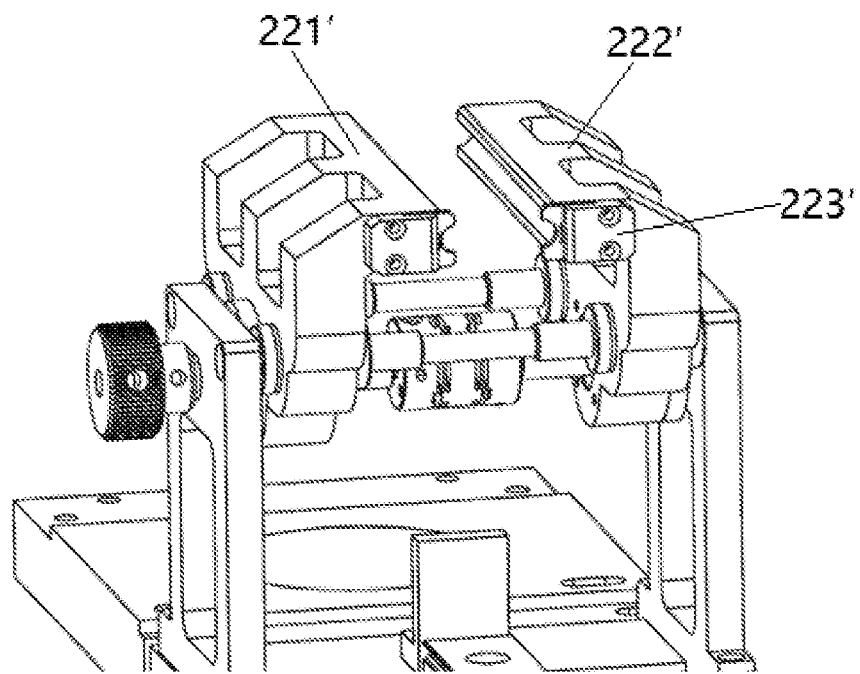
FIG. 15 illustrates the structure of a second embodiment of a gripping mechanism of the device according to the present invention.
Figure 16:
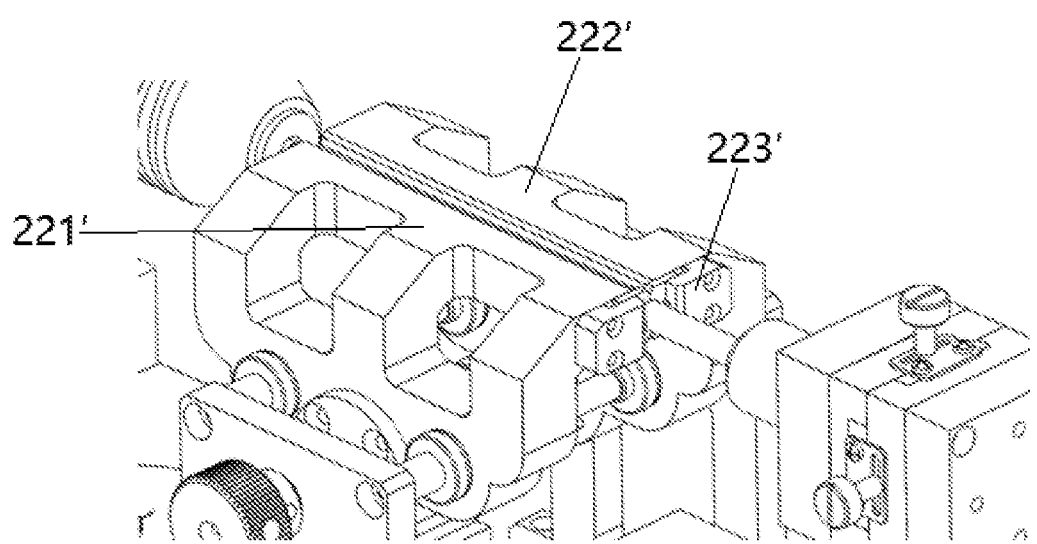
FIG. 16 illustrates the structure of a second embodiment of a gripping mechanism when gripping the lumen tissue of the device according to the present invention.

Specifically or further, as shown in FIGS. 13-16, the gripping mechanism 22 includes a first gripping block 221, 221' and a second gripping block 222, 222' which are movable relatively. As shown in FIGS. 13 and 14, the relative movement of the first gripping block 221 and the second gripping block 222 may be preferably realized by providing a guide rail. As shown in FIGS. 15 and 16, the relative movement of the first gripping block 221' and the second gripping block 222' may also be preferably realized by providing a leadscrew nut mechanism. Even further, as shown in FIG. 14, the gripping mechanism 22 further includes a limiting block 225 provided at the bottom of the first gripping block 221 and the second gripping block 222, for limiting relative movement of the first gripping block 221 and the second gripping block 222, so that the first gripping block 221 and the second gripping block 222 are both tangent to the outer wall of the lumen tissue, and it is possible to produce certain limiting effect for the lumen tissue during assembling the artificial tissue precursor.

In order to ensure that the lumen tissue is removed from the hollow rod 231 as much as possible, in one further embodiment, as shown in FIGS. 13 to 16, the gripping mechanism 22 further includes a retaining unit 223, 223' for acting on a tail end of the lumen tissue so that it is disengaged from the hollow rod 231 to prevent the lumen tissue from following the hollow rod 231 when the hollow rod 231 is displaced in an opposite direction. The retaining units 223, 223' may be disposed at a tail end of the first gripping blocks 221, 221' and/or the second gripping blocks 222, 222', and may also be directly disposed on the gripping mechanism independent of the first gripping block and the second gripping block. Even further, the retaining unit 223 is cooperatively provided with a retaining ring acting on the tail end of the lumen tissue, so that the lumen tissue is more easily disengaged from the hollow rod 231. Still further, as shown in FIG. 14, the gripping mechanism 22 further includes a support platform 224 provided at the bottom of the first gripping block 221 and the second gripping block 222, for supporting the lumen tissue. In the process of the lumen tissue socketing the biological construct, the support platform 224 is exactly tangent to the outer wall at the bottom of the lumen tissue, for providing an upward force for the lumen tissue and avoiding the sinking of the lumen tissue.

In an improved embodiment of device for printing the lumen tissue construct of the present invention, the device further comprises a reservoir provided below the rotary rod 211, for bearing a bioprinting construct disengaged and falling from the gripping mechanism 22. After the printing assembly is completed, the bioprinting construct is gripped by the gripping mechanism 22, and an entirety of the rotary rod 211 is withdrawn towards an opposite direction. The bioprinting construct is located immediately above the reservoir, and is supported by the gripping mechanism 22. At this time, the gripping mechanism 22 withdraws the gripping force, so that the bioprinting construct falls vertically into the reservoir. This design can avoid the introduction of new contamination in the transfer operation process implemented manually or by robotic arm after the completion of printing, or the damage caused for printing the inner wall of a blood vessel due to inappropriate operation in the operational process, and facilitate the packaging of a finished product.

The present invention correspondingly provides a method for printing lumen tissue construct using the aforementioned device, which comprises a mantling step: cladding a layer of elastic film on the outer wall of the rotary rod 211 before printing the biological construct. During the printing of the biological construct, the elastic film presents a natural state, and clads on the surface of the rotary rod 211. The bio-block makes up a biological construct on the surface of the elastic film, thus favorable for removing the biological construct. Further, the printing method of the lumen tissue construct printing device further comprises a film ballooning step: ventilating into the elastic film to balloon the elastic film so that the biological construct is attached to the inner wall of the lumen tissue, after the lumen tissue is sleeved outside the biological construct. The biological construct on the surface of the elastic film is displaced outwards along with the expansion of the elastic film, and finally in contact with the inner wall of the lumen tissue and adhered onto the inner wall of the lumen tissue, so that the biological construct is completely evenly, intactly, and flatly attached on the inner wall of the lumen tissue, such as to obtain an artificial tissue precursor. It is demonstrated in practice that, the embodiment is easy to operate and implement, and presents a high implementability.

Next, the construction process of the artificial tissue precursor of the lumen tissue construct printing device of the present invention is explained by exemplifying the embodiments shown in FIGS. 1 to 14 as follows:

The bio-ink constructs a biological construct on the surface of the elastic film by means of the bio-block sprayhead 12, and then a medical adhesive layer for adhering the bio-block and the lumen tissue is uniformly extruded on the surface of the biological construct by means of the medical adhesive sprayhead 11.

After the biological construct is made, the hollow rod 231 moves toward the rotary rod 211 until the hollow rod 231 is completely sleeved outside the rotary rod 211. At this time, the lumen tissue is completely outside the biological construct, and the hollow rod 231 moves towards a direction away from the rotary rod 211, then the gripping mechanism 22 prevents the lumen tissue from following the movement of the hollow rod 231. Finally, the hollow rod 231 is completely separated from the rotary rod 211, but the lumen tissue remains outside the biological construct. Limited by the mechanical structure, there is inevitably a gap between the lumen tissue and the biological construct at this time, then an upward force is provided to the lumen tissue by means of the support platform 224, so as to avoid uneven attachment between the biological construct and the artificial blood vessel resulting from a downward movement due to the effect of gravity. Then, the rotary rod 211 is internally ventilated to balloon the elastic film, so that the biological construct is completely attached onto the inner wall of the lumen tissue. The heating unit 212 heats to accelerate the coagulation of the bio-ink, to finally obtain an artificial tissue precursor, which is removed from the rotary rod 211.

Since the printed artificial tissue precursor needs to detect the flatness of its inner wall, in an improved embodiment of the device for printing lumen tissue construct of the present invention, the device may further comprise an optical probe movable inside the rotary rod 211, for detecting the flatness of the inner wall of the biological construct, wherein the rotary rod 211 is made of a transparent material. There is a high implementability to design the optical probe in such a form as to be movable inside the rotary rod 211, and to move the optical probe and photograph the internal wall of the biological construct by an image acquisition software before the artificial tissue precursor is removed from the rotary rod 211, so as to judge whether the printed bio-block coating is intact, smooth and flat or not, and the embodiment adequately utilize the hollow structure inside the rotary rod 211 to improve the structural utilization rate, which presents a high implementability.

For how to effectuate that the optical probe is movable inside the rotary rod 211, in some improved embodiments, the optical probe is fixedly disposed in the hollow rod 231. For example, the hollow rod 231 is designed in a double-layer embedded structure, in which the first layer is used for embedding an artificial blood vessel, and the front end of the second layer is provided with an optical probe. The rotary rod 211 may also be a double-layer structure, in which ventilation is performed within the sandwich for ballooning the elastic film. The elastic film only covers the surface of the rotary rod 211 but does not cover the front end, such as to enable the optical probe to extend into the rotary rod 211. In the assembly process, the lumen tissue is sleeved on the surface of the biological construct, and the optical probe also moves along with the hollow rod 231 to the furthest end of the biological construct. When the lumen tissue is removed, the optical probe also moves along with the hollow rod 231 to the foremost end of the artificial precursor tissue, so as to accomplish the flatness detection in the assembly process. Certainly, in other improved embodiments, the optical probe is movably disposed in the hollow rod 231, that is, the optical probe moves independently with respect to the hollow rod 231, and the flatness detection can also be accomplished. In some other modified embodiments, the optical probe is movably disposed in the rotary rod 211, and the optical probe moves from one end to the other within the rotary rod 211 to accomplish the flatness detection.

The present invention further provides a 3D bioprinter, which comprises the aforementioned device for printing lumen tissue construct. As the device of the present invention can improve the biological reliability of the lumen tissue, correspondingly, the 3D bioprinter of the present invention also has the advantageous technical effects described above, and thus will no longer be repeated here.

The above-combined embodiments make detailed explanations for the embodiments of the present invention, but the present invention is not limited to the embodiments described. For a person skilled in the art, multiple changes, modifications, equivalent replacements, and variations made to such embodiments still fall within the protection scope of the present invention without departing from the principles and substantive spirit of the present invention.

What is claimed is:

1. A device for printing lumen tissue construct, comprising a sprayhead assembly and a bioprinting platform, wherein the sprayhead assembly is for printing a biological construct on an inner surface of a lumen tissue by the bioprinting platform; and wherein the sprayhead assembly includes a bio-block sprayhead which consists of a screw pump and a bio-block nozzle, and the screw pump includes a spiral stator and a spiral rotor for extruding a bio-block entering the screw pump to the bio-block nozzle.

2. The device of claim 1, wherein the sprayhead assembly includes a medical adhesive sprayhead, which consists of a medical adhesive container and a medical adhesive nozzle, and the device further includes an air pump, an air path and a vacuum generator; and wherein a top of the medical adhesive container is connected with the air pump through the air path, and the vacuum generator is provided in the air path for generating a negative pressure for the medical adhesive container in a non-printing state.

3. The device of claim 1, wherein the spiral stator is made of a silicone material.

4. The device of claim 1, wherein the bio-block nozzle includes a printing outlet end, the printing outlet end of the bio-block nozzle has a chamfer, and a chamber, wherein the chamber has a chamfered surface defining an included angle of 10° to 30° with a center line of a printing outlet of the bio-block nozzle.

5. The device of claim 4, wherein the included angle is 20°.

6. The device of claim 1, wherein an outer surface at a printing outlet end of the bio-block nozzle has a roughness Ra≤0.4.

7. The device of claim 1, wherein;

the bioprinting platform includes a platform base, a rotary part and a butt-jointed part movable relative to the rotary part, the rotary part includes a rotary rod for placing a bio-block and a medical adhesive to form a biological construct, and the butt-jointed part includes a hollow rod having an outer wall for placing lumen tissue.

8. The device of claim 7, wherein the outer wall of the rotary rod is covered with an elastic film.

9. The device of claim 8, wherein an interior of the rotary rod is hollow, and the outer wall of the rotary rod is provided with a vent communicating with the interior, for exhausting air inside the rotary rod to balloon the elastic film.

10. The device of claim 7, wherein an interior of the rotary rod is provided with a heating unit.

11. The device of claim 10, wherein the heating unit includes a heating section and a spacing section that are spacedly arranged, the heating section has a surface wound with a resistance wire, and the heating section has a diameter that is less than that of the spacing section.

12. The device of claim 10, wherein a temperature detecting unit is provided at one end of the heating unit proximate to the butt-jointed part, for detecting a temperature of the heating unit.

13. The device of claim 7, wherein the bioprinting platform includes a gripping mechanism for gripping the lumen tissue to make the lumen tissue disengaged from the hollow rod and socketed to the biological construct.

14. The device of claim 13, wherein the gripping mechanism includes a first gripping block and a second gripping block which are movable relatively.

15. The device of claim 14, wherein the gripping mechanism includes a retaining unit for acting on a tail end of the lumen tissue so that the lumen tissue is disengaged from the hollow rod.

16. The device of claim 15, wherein the retaining unit is cooperatively provided with a retaining ring acting on the tail end of the lumen tissue.

17. The device of claim 14, wherein the gripping mechanism includes a limiting block provided at a bottom of the first gripping block and the second gripping block, for limiting relative movement of the first gripping block and the second gripping block, so that the first gripping block and the second gripping block are both tangent to an outer wall of the lumen tissue.

18. The device of claim 14, wherein the gripping mechanism includes a support platform provided at a bottom of the first gripping block and the second gripping block, for supporting the lumen tissue.

19. The device of claim 13, further comprising a reservoir provided below the rotary rod, for bearing a bioprinting construct disengaged and falling from the gripping mechanism.

20. The device of claim 7, further comprising an optical probe movable inside the rotary rod, for detecting a flatness of an inner wall of the biological construct, wherein the rotary rod is made of a transparent material.

21. The device of claim 20, wherein the optical probe is movably disposed within the rotary rod or the hollow rod.

22. The device of claim 20, wherein the optical probe is fixedly disposed within the hollow rod.

23. A method of printing lumen tissue construct using the device of claim 7, comprising a mantling step comprising: cladding a layer of elastic film on an outer wall of the rotary rod before printing the biological construct.

24. The method of claim 23, further comprising a ballooning step comprising: ventilating into the layer of elastic film to balloon the layer of elastic film so that the biological construct is attached to the inner surface of the lumen tissue, after the lumen tissue is sleeved outside the biological construct.

25. A 3D bioprinter comprising the device of claim 1.

* * * * *